United States Patent [19]

Foster

[11] 4,325,880

[45] Apr. 20, 1982

[54] PROCESS FOR CONVERSION OF STEROL I-METHYL ETHERS TO STEROLS

[75] Inventor: Charles H. Foster, Kingsport, Tenn.

[73] Assignee: Eastman Kodak Company, Rochester, N.Y.

[21] Appl. No.: 250,811

[22] Filed: Apr. 3, 1981

[51] Int. Cl.³ .............................................. C07J 9/00
[52] U.S. Cl. ................................................. 260/397.2
[58] Field of Search ..................................... 260/397.2

[56] References Cited

U.S. PATENT DOCUMENTS

| | | | |
|---|---|---|---|
| 3,038,272 | 7/1977 | Partridge, Jr. et al. | 260/397.2 |
| 4,224,230 | 9/1980 | DeLuca et al. | 260/397.2 |
| 4,260,549 | 4/1981 | DeLuca et al. | 260/397.2 |

*Primary Examiner*—Elbert L. Roberts
*Attorney, Agent, or Firm*—Clyde L. Tootle; Daniel B. Reece, III

[57] ABSTRACT

The present invention discloses a simple process for converting sterol i-methyl ethers to sterols. More particularly, the invention is directed to a process for converting sterol i-methyl esters to the corresponding sterols by refluxing the sterol i-methyl ethers in aqueous acetic acid to provide conversion to sterols at high yields. This provides a simple process for converting sterol i-methyl ethers to sterols which can be important for preparing valuable steroids such as the corticosteroids.

5 Claims, No Drawings

PROCESS FOR CONVERSION OF STEROL I-METHYL ETHERS TO STEROLS

The present invention discloses a simple process for converting sterol i-methyl ethers to sterols. More particularly, the invention is directed to a process for converting sterol i-methyl ethers to the corresponding sterols by refluxing the sterol i-methyl ethers in aqueous acetic acid to provide conversion to sterols at high yields.

It is known in the art to prepare the sterol i-methyl ethers to block or protect the A and B rings of sterols in various synthesis procedures. For, example, the conversion to the i-methyl ether protects the hydroxyl group in the 3 position of the A ring and the unsaturated group in the 5,6 positions of the B ring. The phytosterol-i-methyl ethers canbe prepared according to the procedure disclosed in U.S. Pat. No. 4,192,811, for example. After the synthesis reactions and modifications of the steroidal molecule is completed, it is generally necessary to convert the steroid i-methyl ether back to the hydroxyl group of the sterol. Prior art processes, for making this conversion are, for example, the process as disclosed in U.S. Pat. No. 4,038,272. This prior art process requires that the conversion be carried out by the use of a strong acid such as sulfuric acid, and comparative large amounts of solvent, such as dioxane, and thereafter extraction and washing with large amounts of aqueous caustic solutions. It would, therefore, be an advance in the state of the art to provide a simple one-step process using a small amount of reagents to convert sterol-i-methyl ethers to sterols in high yield.

In accordance with the present invention, a sterol i-methyl ether is refluxed in aqueous acetic acid for a period of about one hour. The amount of aqueous acetic acid is generally from four to ten times the amount of sterol i-methyl ether to be converted in order to obtain maximum conversion. After conversion, the reaction mixture is cooled to 15°–25° C. Upon addition of water, the hydroxyl group containing sterols are separated by filtration and washed with water.

The amount of aqueous acetic acid used is generally about 3 to 10 times the weight percent of i-methyl ether to be converted. This provides sufficient aqueous acetic acid to completely dissolve the i-methyl ether at the refluxing temperature.

The amount or concentration of acetic acid relative to the water in the aqueous acetic acid can be varied from about 99 to 50 weight percent acetic acid to 1 to 50 percent, by weight, water. At least one mole percent of water is necessary to provide the hydroxyl group of the product sterol. The more preferred concentration is about 99 to 70 percent acetic acid to 1 to 30 weight percent water, most preferred 85 to 75 weight percent acid to 15 to 25 weight percent water and the most preferred about 80 weight percent acetic and about 20 weight percent water.

The time necessary to carry out the conversion generally is about 2 to 20 hours. The time necessary depends on the solubility of the i-methyl ether in the aqueous acetic acid and the temperature. Using aqueous acetic acid containing 80:20 acetic acid:water provided good solubility and conversion in about 2.5 hours.

After conversion, the mixture is cooled to ambient temperature. An amount of water is added which causes the converted sterol to precipitate and be recovered by filtration. The amount of water added depends on the amount of water in the aqueous acetic acid. An aqueous acid containing 50:50 acetic acid:water generally precipitates on cooling to room temperature with no further addition of water. Aqueous acetic acid containing 90:10 weight percent acetic acid:water will require some water to be added for complete precipitation.

This invention can be further illustrated by the following examples, although it will be understood that the examples are included merely for purposes of illustration and are not intended to limit the scope of the invention unless otherwise specifically indicated.

EXAMPLE 1

Mixed sitosterol and campesterol i-methyl ethers (19 g) and 100 ml of aqueous acetic acid (80:20 acetic acid-water) were refluxed for 2.5 hours. The mixture was cooled to ambient temperature, water was added and 16.5 g of a mixture of sitosterol and campesterol was recovered by filtration.

EXAMPLE 2

Stigmasterol i-methyl ether (19 g) and 100 ml of aqueous acetic acid (80:20 acetic acid:water) were refluxed for 2.5 hours, and after cooling to ambient temperature, water was added, and 16.5 g of stigmasterol was recovered by filtration.

The process of the present invention provides a simple method for converting sterol i-methyl ethers to sterols. This process is an important method which can be used for preparing valuable steroids such as the corticosteroids.

I claim:

1. A process for converting i-methyl ether steroids to sterols comprising refluxing said i-methyl ether steroids in an aqueous acetic acid containing about 99 to 50 weight percent acetic acid to 1 to 50 percent by weight water for a period of about 2 to 20 hours.

2. A process according to claim 1 wherein said aqueous acetic acid contains 85 to 75 weight percent acetic acid to 15 to 25 weight percent water.

3. A process according to claim 2 wherein said aqueous acetic acid contains about 80 weight percent acetic acid to 20 weight percent water.

4. A process according to claim 3 wherein said process is carried out for a period of 2.5 hours.

5. A process according to claim 4 wherein said i-methyl ether steroids comprises at least one member of the group consisting of i-methyl ether of sitosterol, i-methyl ether of stigmasterol and i-methyl ether of campesterol.

* * * * *